US007192905B1

(12) United States Patent
Li et al.

(10) Patent No.: US 7,192,905 B1
(45) Date of Patent: Mar. 20, 2007

(54) ORGANOPHOSPHATE INSECTICIDE SYNERGISTS FOR FLY AND TICK CONTROL

(75) Inventors: Andrew Y. Li, Kerrville, TX (US); John Allen Miller, Kerrville, TX (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 242 days.

(21) Appl. No.: 10/600,360

(22) Filed: Jun. 20, 2003

(51) Int. Cl.
*A01N 43/70* (2006.01)
*A01N 57/02* (2006.01)
*A01P 7/04* (2006.01)

(52) U.S. Cl. .................. 504/127; 504/133; 504/134; 514/87; 514/89; 514/100; 514/128

(58) Field of Classification Search .............. 504/127, 504/133, 134; 514/87, 89, 100, 128
See application file for complete search history.

(56) References Cited

OTHER PUBLICATIONS

Geiszler-Jones, Amy, "On The Toxic Trail", vol. 16, No. 17, May 11, 2000 Issue; Inside WSU, News Inside, http://www.witchita.edu/insidewsu/@5-11-2000/Lydy_research.htm, [retrieved Jun. 10, 2003].

Jin-Clark, Ying, et al., Atrazine-mediated alterations of gene expression in *Chironomus tentans* (Diptera:Chironomidae), Monday, Dec. 10, 2001—D0031, The ESA 2001 Annual Meeting—2001: An Entomological Odyssey of Esa; http://esa.confex.com/esa/2001/techprogram/paper_3442.htm. [retrieved Jun. 10, 2003].

SIUC Fisheries and Illinois Aquatic Center, SIUC Fisheries and Illinois Aquatic Center Research in Fish Pathology, Current Fish Pathology Research Projects at SIUC—Mike Lydy; http://131/230/57.1/fishweb/pathololgy.htm, [retrieved Jun. 10, 2003].

Zhu, Dr. Kun Yan, homepage, Kansas State Department of Entomology, http://www.oznet.ksu.edu.entomology/faculty/zhu.htm; [retrieved Jun. 10, 2003].

Rabert William et al., "EFED Review of Public Commentsin Response to the EPA EFED Revised Environmental Risk Assessment of Atrazine", United States Environmental Protection Agency, Apr. 10, 2002.

Lichtenstein, E.P., et al., "Synergism of Insecticides by Herbicides", Science, vol. 181, pp. 847-849, Aug. 31, 1973.

Pape-Lindstrom, Pamela A., et al., "Synergistic Toxicity of Atrazine and Organophosphate Insecticides Contravenes The Response Addition Mixture Model", Environ. Toxicol. Chem., 16, 1997, pp. 2415-2420.

Belden, Jason B., et al., "Impact of Atrazine on Organophosphate Insecticide Toxicity", Environmental Toxicology and Chemistry, vol. 19, No. 9, pp. 2266-2274.

Belden, J.B., et al., "Effects of atrazine on acetylcholinestrerase Activity in Midges (*Chironomus tentans*) exposed to organophosphorus insecticides", Chemosphere, 44, 2001, pp. 1685-1689.

*Primary Examiner*—S. Mark Clardy
(74) *Attorney, Agent, or Firm*—John D. Fado; Randall E. Deck; Lesley Shaw

(57) ABSTRACT

Combination of a cytochrome P450 monooxygenase inducer with an organophosphate pesticide (insecticide or acaracide) provides effective control of ticks and flies, particularly against organophosphate-resistant strains of the ticks and flies. In use, a pesticidally effective amount of a composition of the cytochrome P450 monooxygenase inducer and organophosphate pesticide is applied to the locus of the targeted tick or fly.

18 Claims, 21 Drawing Sheets

ORGANOPHOSPHATE INSECTICIDE SYNERGISTS FOR FLY AND TICK CONTROL

BACKGROUND OF THE INVENTION

1. Field of the Invention

The invention relates to a method and compositions for controlling flies and ticks.

2. Description of the Prior Art

Ticks and flies pose a significant risk to the health and welfare of warm-blooded animals, and their resistance to approved acaracides and insecticides threatens efforts to control these pests in the U.S. and elsewhere.

For instance, cattle fever ticks (*Boophilus microplus* and *B. annulatus*) are vectors of protozoan parasites of the genus *Babesia* which are the causative agents of babesiosis and which infect a wide range of vertebrate hosts, including bovine and man. Bovine babesiosis or cattle fever is a particularly serious disease of livestock and domestic animals which historically caused major losses to the cattle industry in the United States. Those losses prompted the U.S. Congress to initiate the Cattle Fever Tick Eradication Program in 1906, which eventually led to the elimination of the cattle fever ticks from the U.S. Unfortunately, tick control efforts in Mexico have not been successful and these ticks remain well established in that country. The reservoir of ticks in Mexico serves as a continuing source of infestation for areas of the U.S. due to the movement of feral, stray, and smuggled animals.

Presently, the cattle tick eradication program relies exclusively on a single organophosphate pesticide, coumaphos, for the treatment of all cattle to prevent the ingress of these ticks into the U.S. However, resistance to coumaphos in Mexican strains of the cattle fever tick *B. microplus* is threatening the continued success of the eradication program.

The horn fly, *Haematobia irritans irritans*, is another blood-feeding pest which poses an increasingly serious threat as the result of the development of insecticide resistant strains. The horn fly is currently one of the most serious pests of cattle in the U.S. When large numbers of these flies are on cattle, the animals will bunch and expend considerable effort fighting the flies, thereby preventing the animals from feeding normally. Studies in the U.S. and Canada have shown that horn fly infested cattle exhibit significantly lower weight gain and reduced milk production than non-infested animals. Traditional methods for control of horn flies have included insecticide-impregnated ear tags, dusting, oiling and spraying animals with various insecticides. At one time, pyrethroids were highly effective, although resistant populations spread rapidly, supplanting the pyrethroid-sensitive populations throughout the U.S. within three years. As a result, more organophosphate pesticides have been used to control horn flies. However, diazinon resistant horn flies have now been found in the U.S., and the failure of horn fly control with diazinon tags has been reported after just three years of use.

As a result of the spread of pesticide-resistant strains of these and other ticks and flies, there is a growing need to develop improved tools for their control.

SUMMARY OF THE INVENTION

We have now discovered that combining a cytochrome P450 monooxygenase inducer with an organophosphate pesticide (insecticide or acaracide) provides effective control of ticks and flies, particularly against organophosphate-resistant strains of the ticks and flies. In use, a pesticidally effective amount of a composition of the cytochrome P450 monooxygenase inducer and organophosphate pesticide is applied to the locus of the targeted tick or fly.

In accordance with this discovery it is an object of this invention is to provide methods and compositions for controlling ticks and flies.

Another object of this invention is to provide methods and compositions for controlling ticks and flies which are resistant to organophosphate pesticides.

A further object of this invention is to provide methods and compositions for controlling ticks and flies which exhibit significantly greater efficacy than those utilizing organophosphate pesticides alone.

Yet another object of this invention is to provide methods and compositions for controlling ticks and flies with reduced amounts of organophosphate pesticides.

Other objects and advantages of this invention will become readily apparent from the ensuing description.

DETAILED DESCRIPTION OF THE INVENTION

Figure 1:
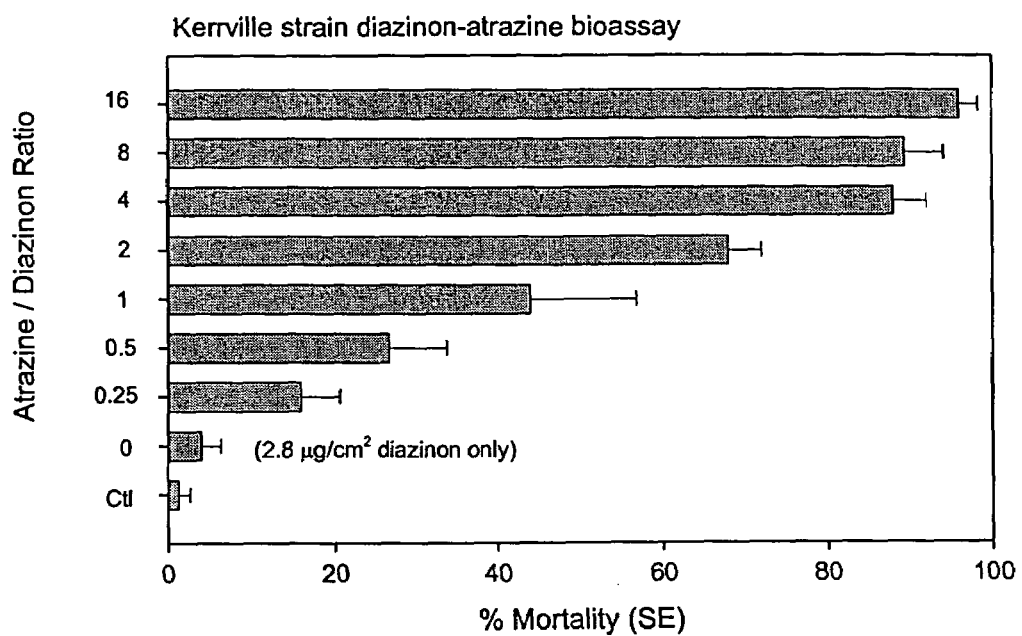
FIGS. 1–8 show the results of Example 1, demonstrating the effect of atrazine and propazine on the toxicity of several organophosphate insecticides/acaracides against the horn fly.
Figure 2:
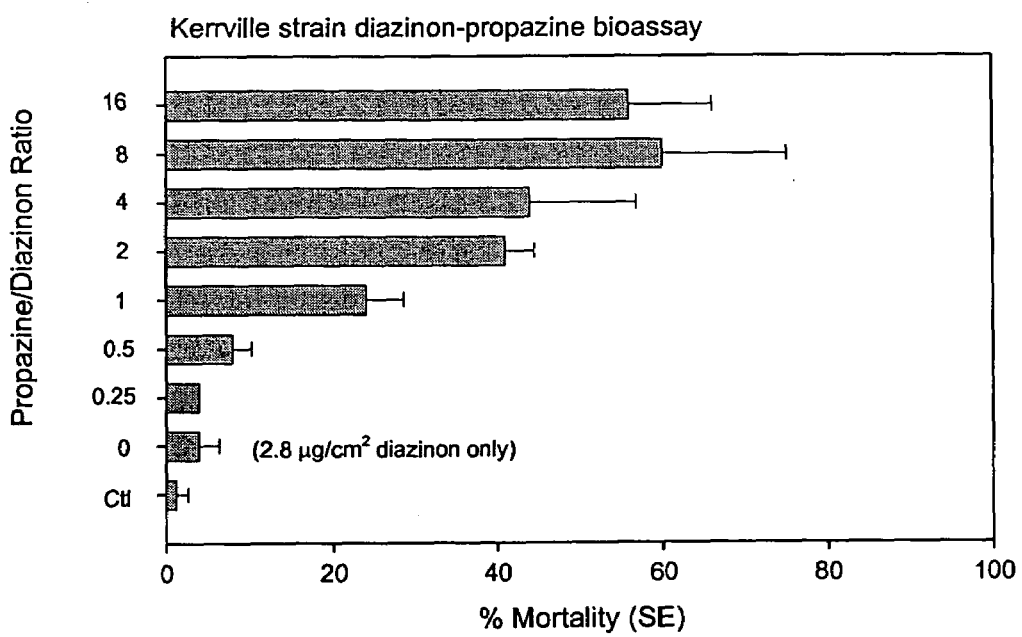
Figure 3:
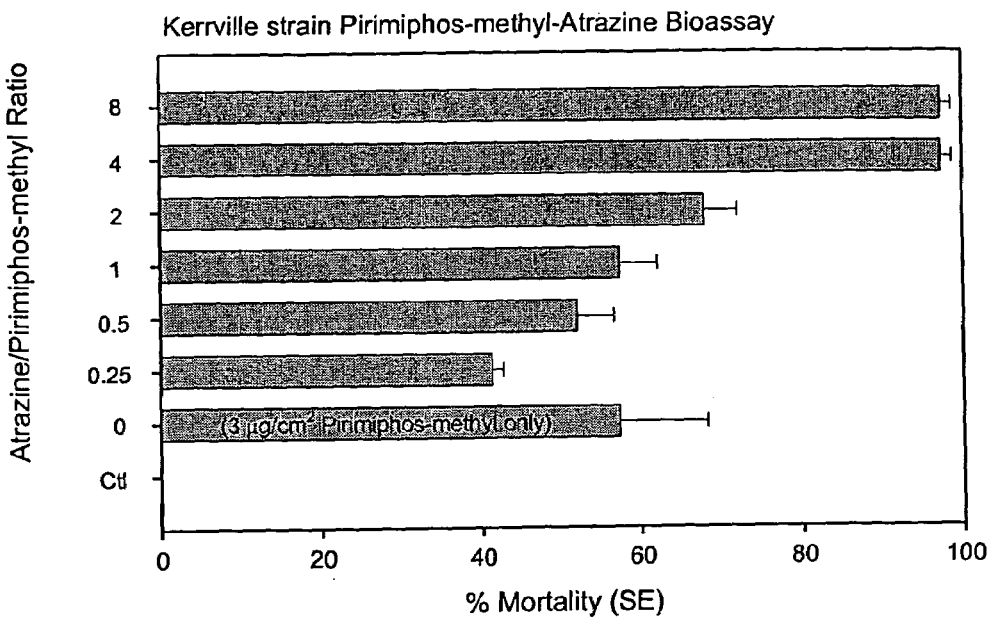
Figure 4:
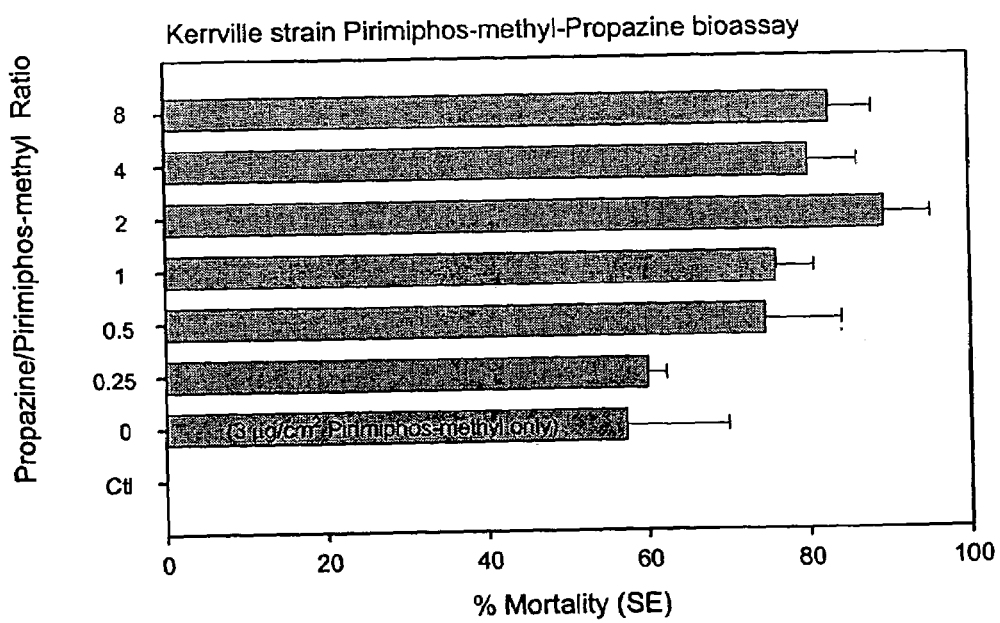
Figure 5:
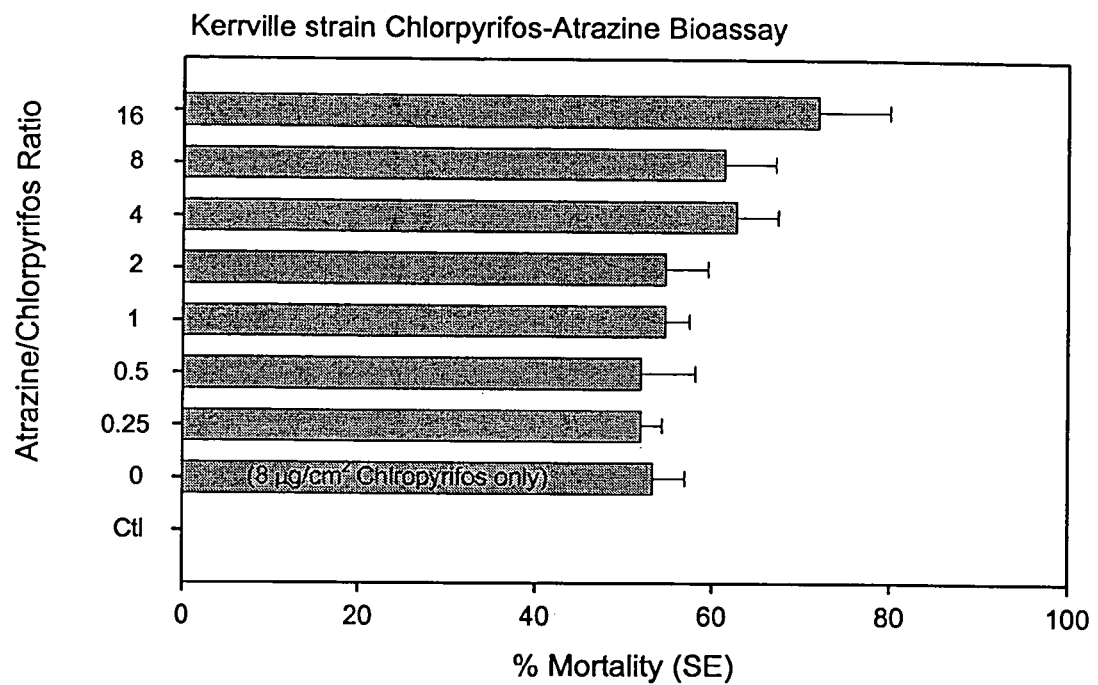
Figure 6:
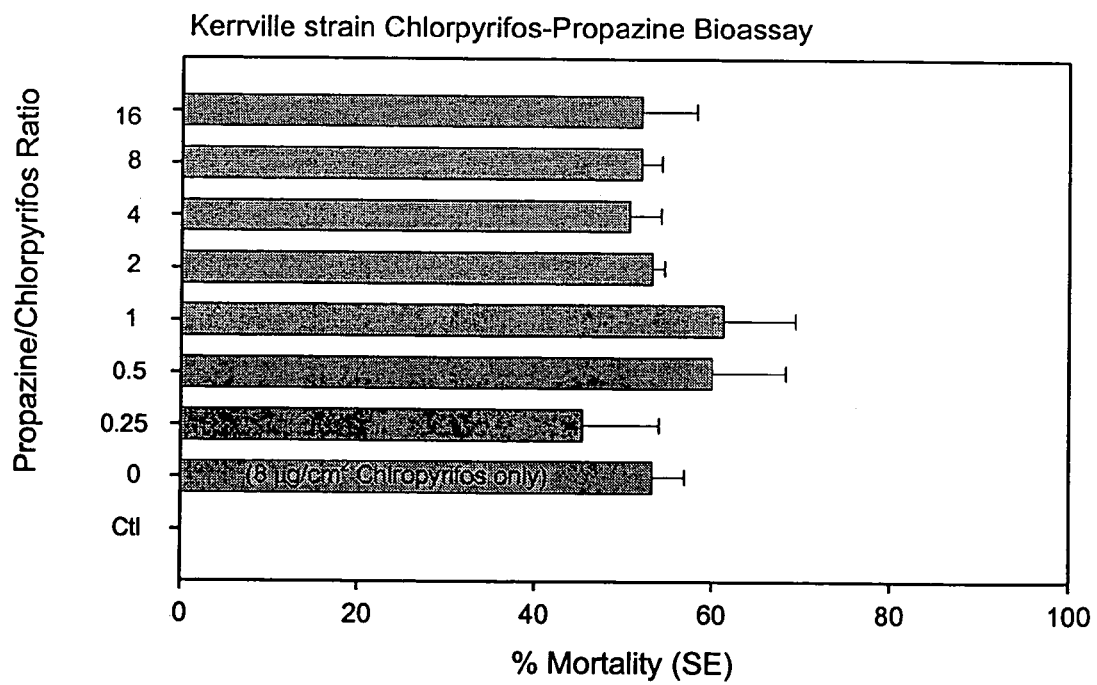
Figure 7:
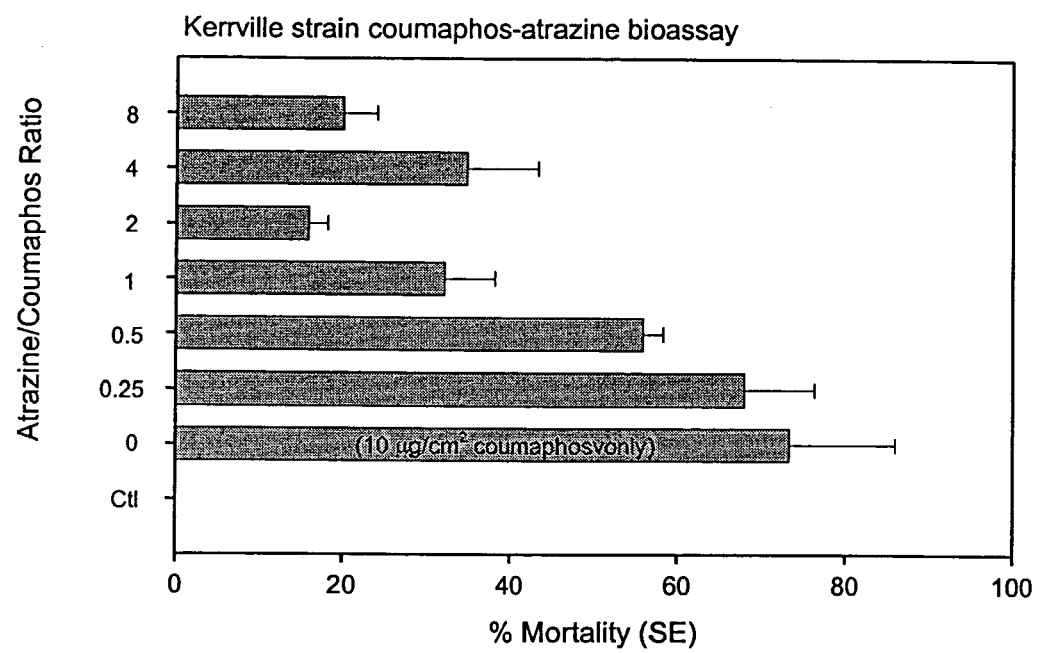
Figure 8:
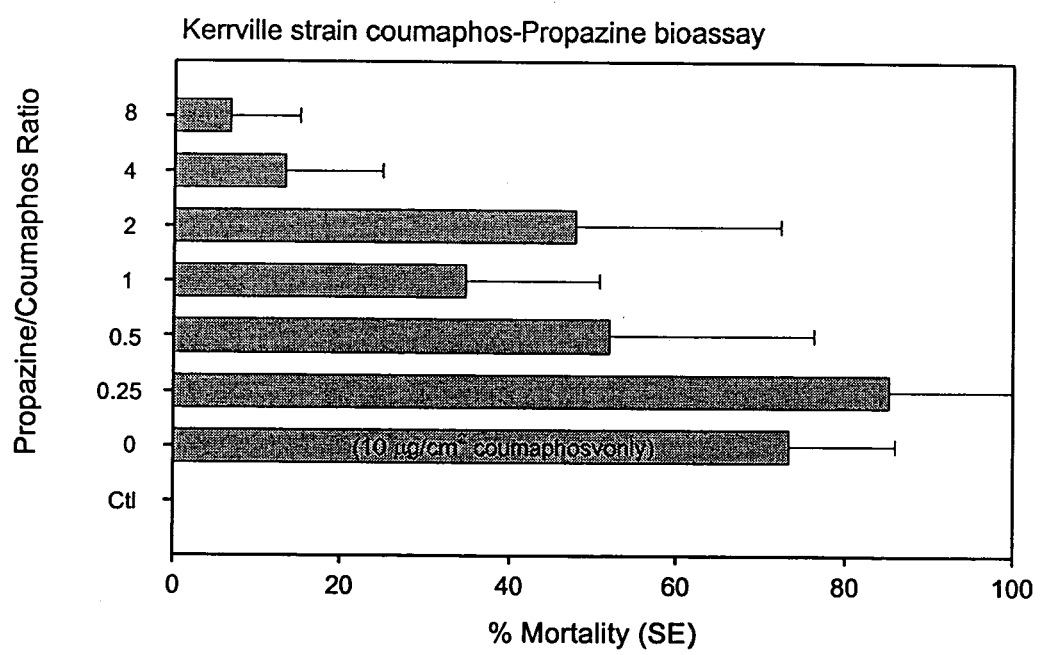
Figure 9:
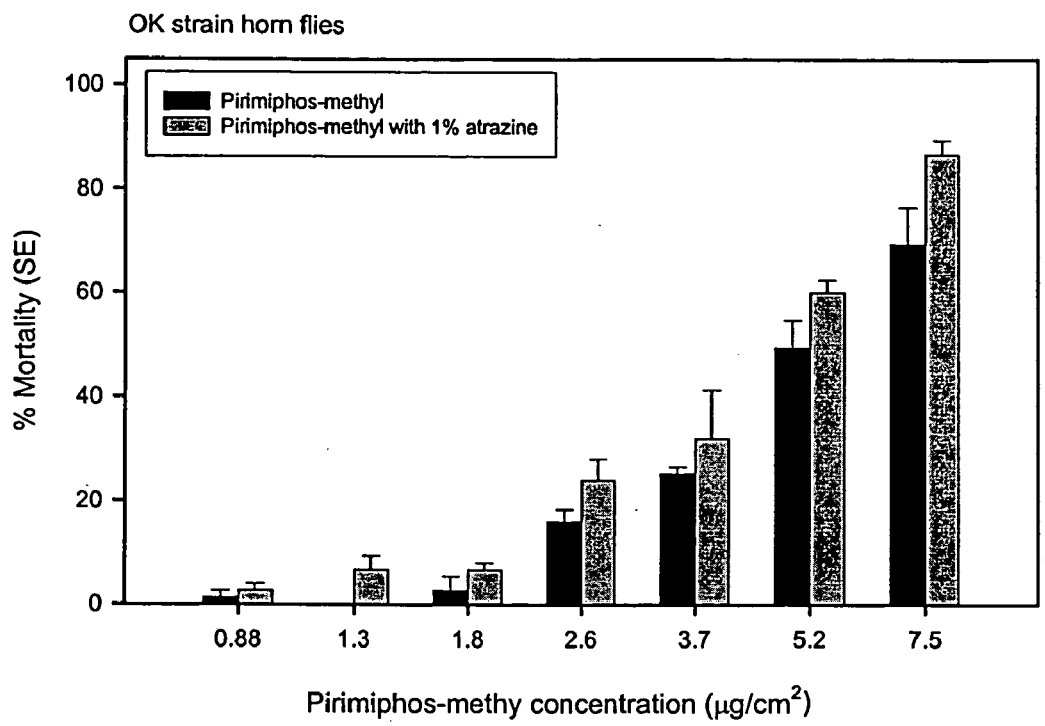
FIGS. 9–18 show the results of Example 2, further demonstrating the effect of atrazine and propazine on the toxicity of several organophosphate insecticides/acaracides against the horn fly.
Figure 10:
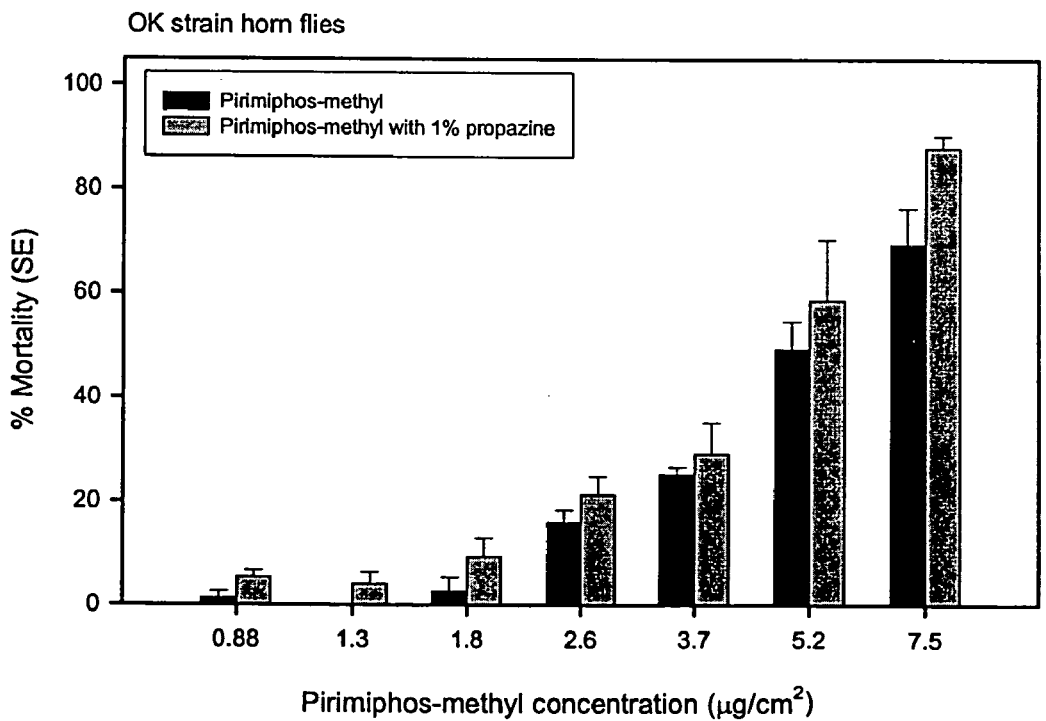
Figure 11:
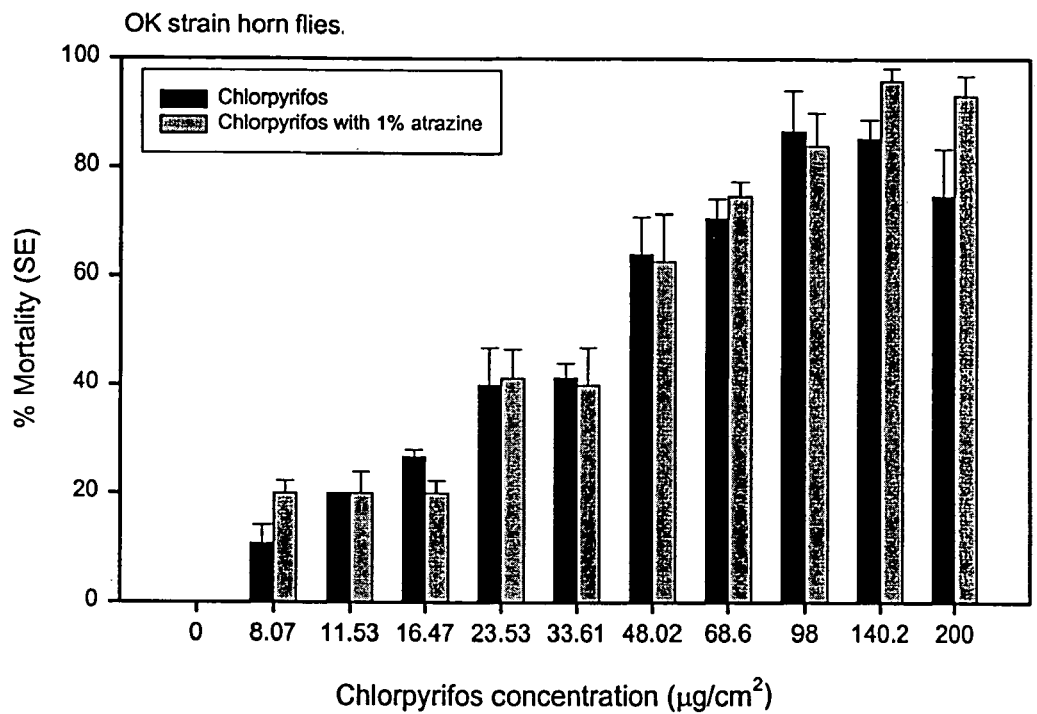
Figure 12:
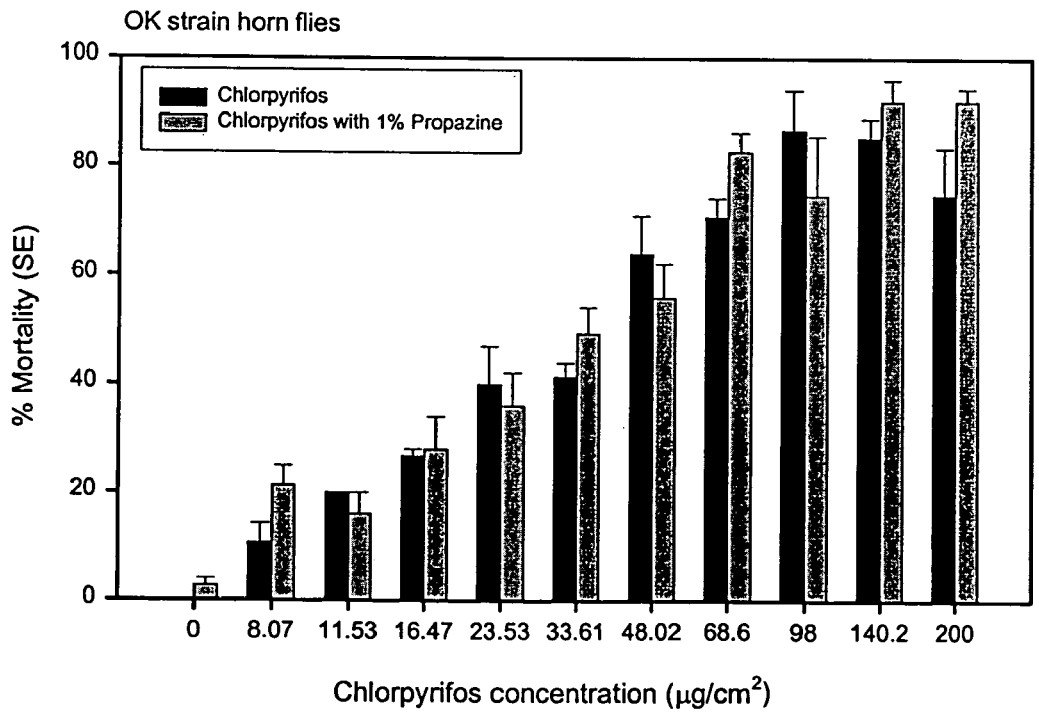
Figure 13:
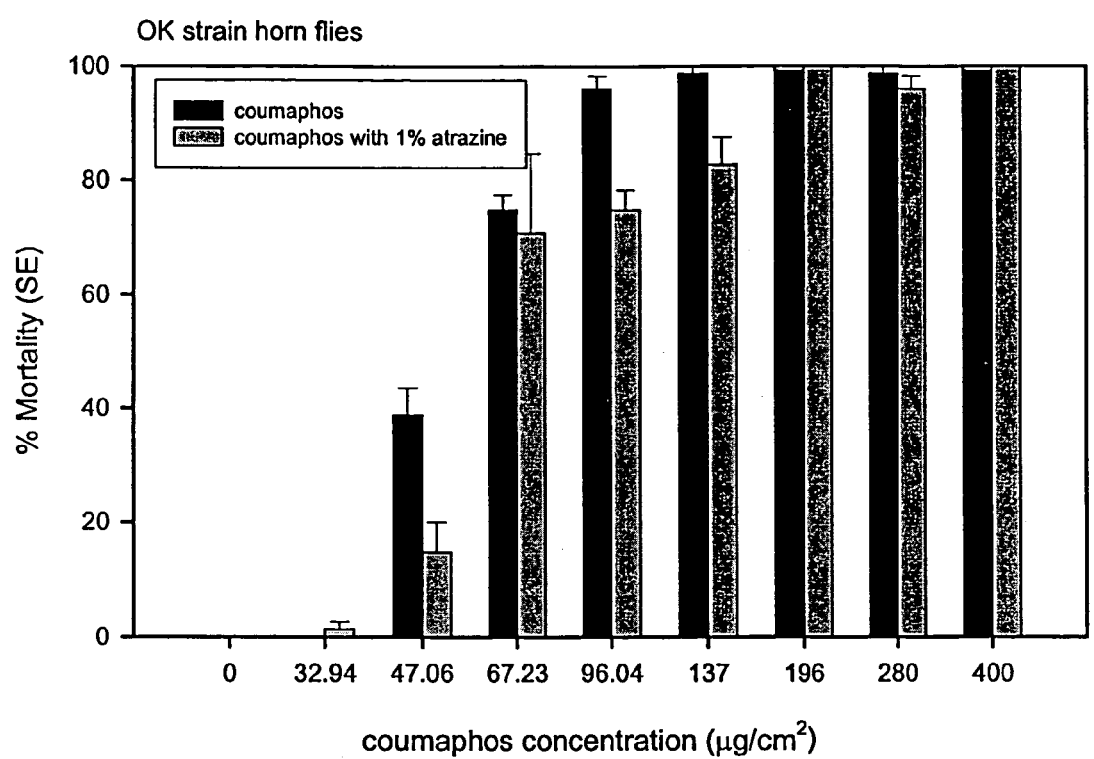
Figure 14:
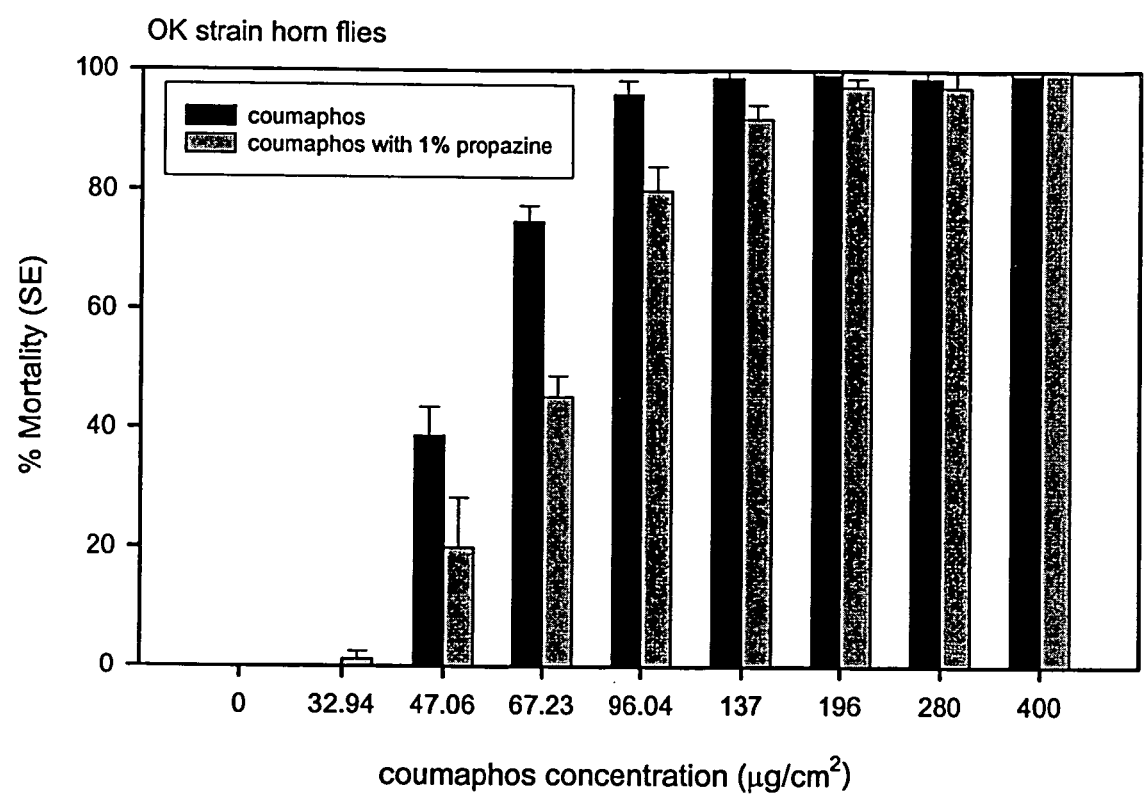
Figure 15:
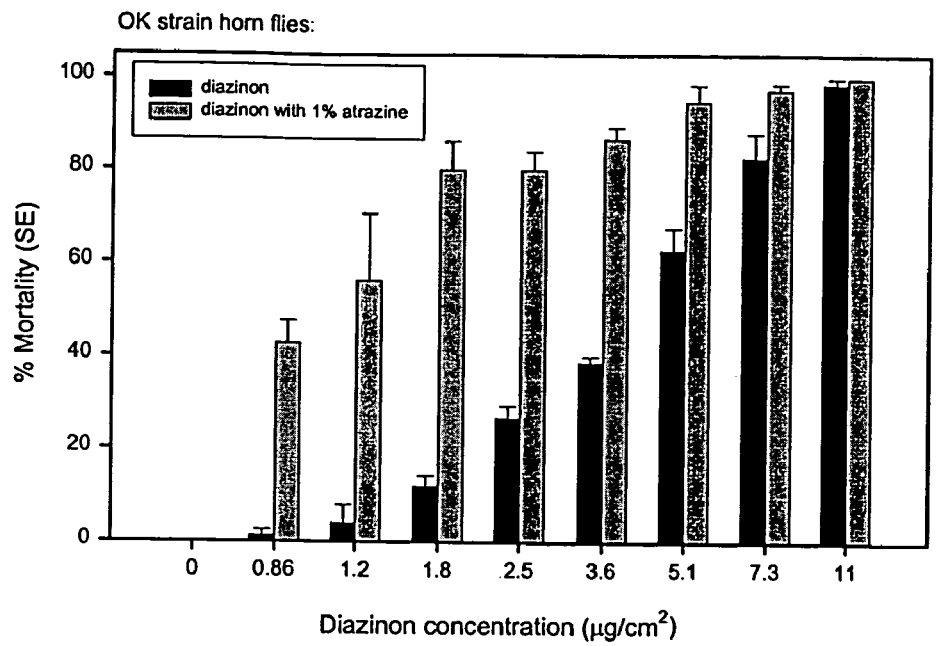
Figure 16:
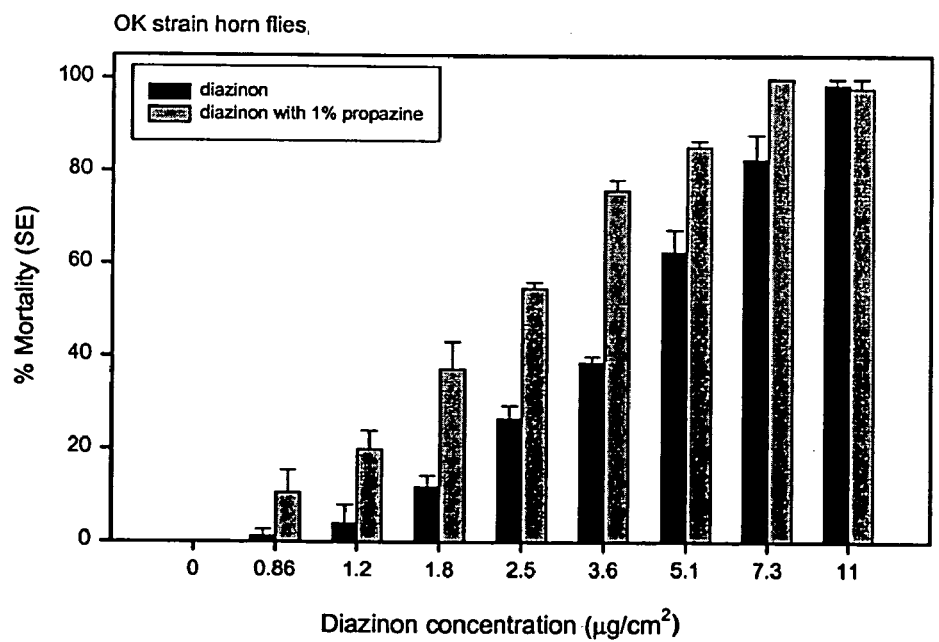
Figure 17:
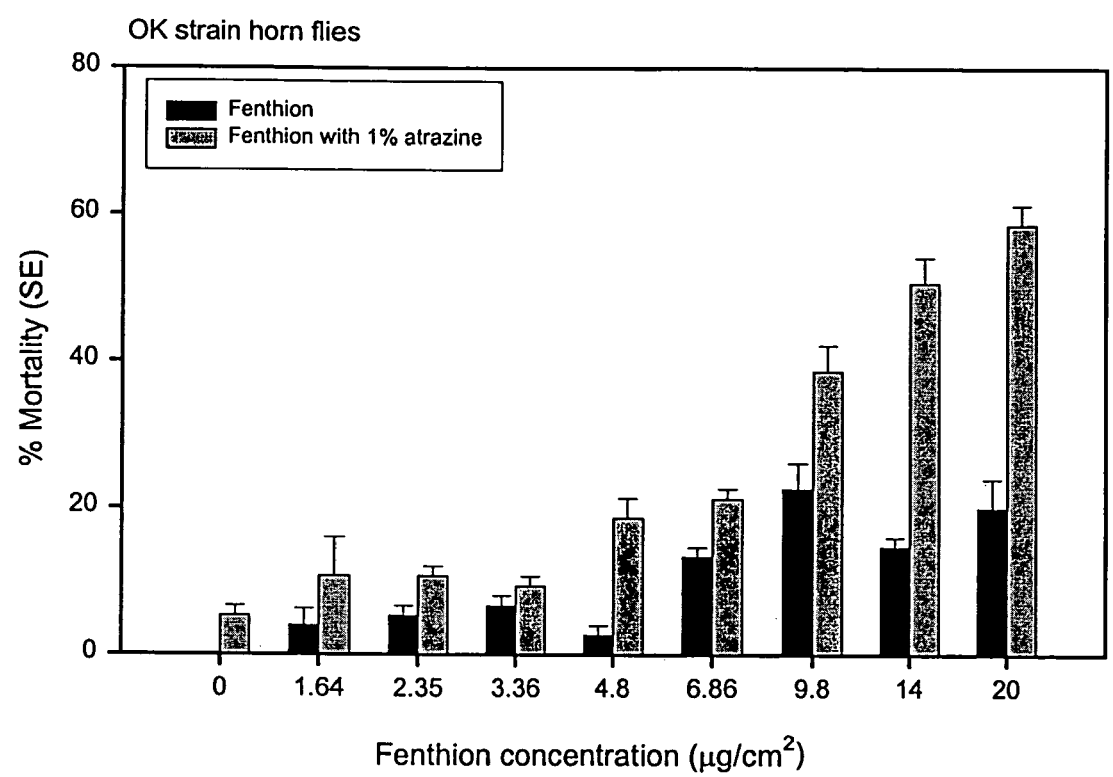
Figure 18:
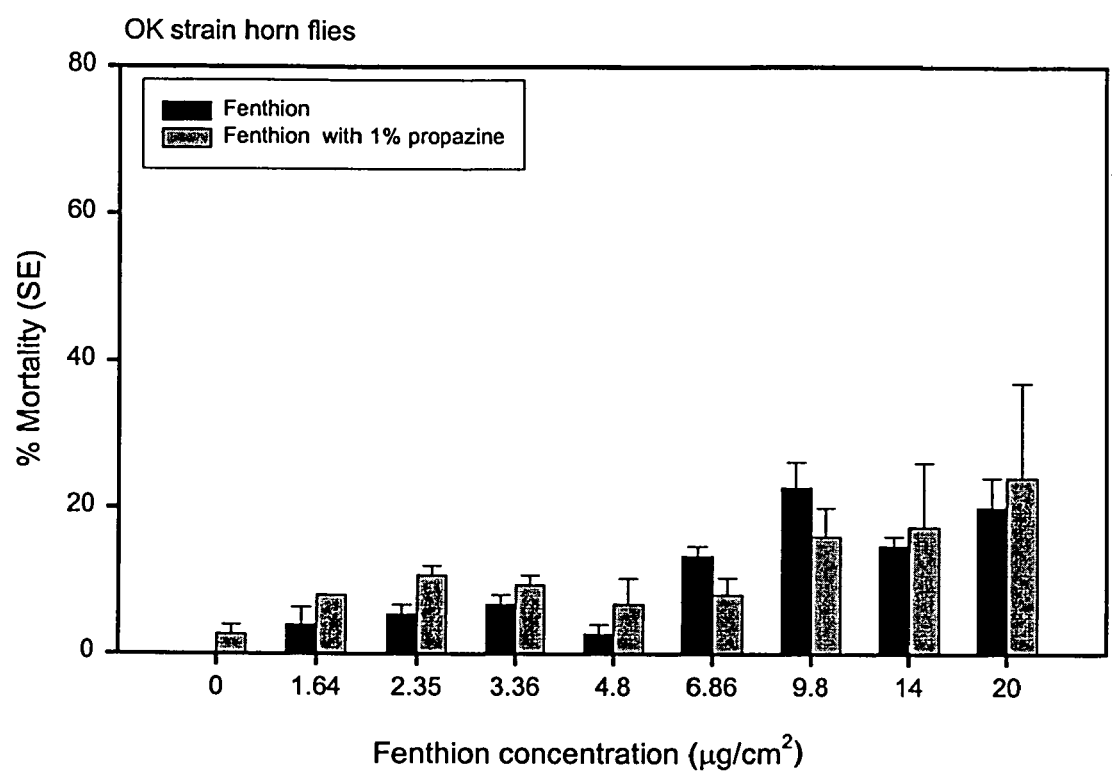

The cytochrome P450 monooxygenase inducer and organophosphate pesticide compositions of the invention are effective for controlling a variety of ticks and flies. Moreover, the compositions are particularly effective for the control of strains of these ticks and flies which are resistant to the organophosphate pesticides alone. The compositions are preferably used for controlling economically important ticks and blood-feeding flies, most notably cattle fever ticks (*Boophilus microplus* and *B. annulatus*), the horn fly (*Haematobia irritans irritans*), and brown dog tick (*Rhipiceph-*

*alus sanuineus*). Without being limited thereto, it is envisioned that the compositions may also be effective for the control of the stable fly (*Stomoxys calcitrans* L.), face fly (*Musca autumnalis*), house fly (*Musca domestics*), and lonestar tick (*Amblyomma americanum*).

In the absence of other insecticidal or acaracidal agents, the cytochrome P450 monooxygenase inducers exhibit poor or no biocidal activity against ticks and flies at low concentrations (i.e., less than or equal to about 1% w/v, wherein 1%=10 mg/ml). However, we have discovered that when the ticks and flies are exposed to organophosphate pesticides in combination with these same cytochrome P450 monooxygenase inducers, the pesticidal activity of the organophosphate pesticides is synergistically increased. As used herein, a synergist is defined as a first material which enhances the activity of other materials, such as organophosphate pesticides, so that the overall activity of the combination is greater than the sum of the individual materials alone.

Suitable cytochrome P450 monooxygenase inducers for use in the invention are therefore those which are effective as synergists for organophosphate pesticides (insecticides or acaracides) against a particular tick or fly of interest. Preferred cytochrome P450 monooxygenase inducers for use herein are triazines, more preferably triazine herbicides including but not limited to chlorinated s-triazines such as atrazine, cyanazine, cyprozine, simazine, procyazine, and propazine, methoxy s-triazines such as atraton, prometon, secbumeton, and simeton, methylthio s-triazines such as ametryn, prometryn, terbutryn, simetryn, and desmetryne, and asymmetrical triazines such as metribuzin, with atrazine, simazine, and propazine being particularly preferred.

A variety of organophosphate pesticides, including both insecticides and acaracides, exhibit a synergistic increase in their pesticidal activity against ticks and flies when they are combined with the cytochrome P450 monooxygenase inducers. Preferred organophosphate pesticides include coumaphos, diazinon, chlorpyrifos, fenthion, and pirimiphos-methyl. However, it is envisioned that other organophosphate pesticides may also be used, including, but not limited to, ethion, phosmet, dimethoate, famphur, dichlorfenthion, chlorpyrifos-methyl, parathion, and methyl-parathion.

As a practical matter it is anticipated that the cytochrome P450 monooxygenase inducer plus organophosphate pesticide compositions will be prepared by formulating the compounds with a suitable inert carrier as known in the art. The compounds may, for example, be formulated as solutions, emulsions, emulsifiable concentrates, suspension concentrates, wettable powders, dusts, granules, adherent dusts or granules, baits, and aerosols. Of greatest interest are those carriers which are agronomically or pharmaceutically acceptable, particularly those suitable for topical application onto animals. The particular carrier selected is not critical, and a variety of liquid and solid phase carriers may be used, including but not limited to water, aqueous surfactant mixtures, alcohols, ethers, hydrocarbons, halogenated hydrocarbons, glycols, ketones, esters, oils (natural or synthetic), clays, kaolinite, silicas, cellulose, rubber, talc, vermiculate, and synthetic polymers. The composition may also be formulated into conventional controlled release microparticles or microcapsules. In addition, the compounds may be optionally formulated with conventional insect and/or tick attractants, pheromones, baits, or other chemical or biological insecticides and/or acaracides.

The organophosphate pesticides of the invention generally act to control pests by killing the targeted tick or fly. Accordingly, the combination of cytochrome P450 monooxygenase inducer plus organophosphate pesticide is administered in an amount effective to induce death of the targeted tick or fly as predetermined by routine testing. An "effective amount" or "pesticidally effective amount" is defined herein to mean those quantities of the composition which will result in a significant mortality rate of a test group as compared to an untreated control group (measured at a confidence level of at least 80%, preferably measured at a confidence level of 95%). Similarly, the amount of the cytochrome P450 monooxygenase inducer within the composition should be effective to provide a synergistic increase the pesticidal activity of the organophosphate pesticide with which it is combined against the targeted tick or fly. A "synergistically effective amount" is therefore defined as that amount of cytochrome P450 monooxygenase inducer which results in a mortality rate in a test group exposed to the combination of cytochrome P450 monooxygenase inducer plus organophosphate pesticide, which is significantly greater than the additive mortality rates in test groups exposed to these same components individually (measured at the same confidence levels as above). Suitable amounts and concentrations may be readily determined by a practitioner skilled in the art, and will vary with the particular species of pest and its strain (i.e. resistant or relatively sensitive to the organophosphate insecticide), its stage of development, the particular organophosphate pesticide and cytochrome P450 monooxygenase inducer synergist, the type of vehicle or carrier, and the period of treatment.

By way of illustration and without being limited thereto, preferred compositions of the invention include atrazine with coumaphos, atrazine with diazinon, atrazine with chlorpyrifos, propazine with diazinon, atrazine with fenthion, atrazine with pirimiphos-methyl, and propazine with pirimiphos-methyl. For the control of organophosphate susceptible cattle fever ticks, suitable concentrations of coumaphos, diazinon, and chlorpyrifos are all greater than or equal to about 0.01% w/v (preferably greater than or equal to about 0.05%), and suitable ratios of cytochrome P450 monooxygenase inducer to the organophosphates are greater than or equal to about 0.5/1 (preferably greater than or equal to about 1/1). In contrast, for control of strains of cattle fever ticks which are or are suspected of being resistant to organophosphates, the amounts are typically increased. Specifically, suitable minimum concentrations of coumaphos, diazinon, and chlorpyrifos are increased to about 0.1, 0.05, and 0.01% (preferably about 0.5, 0.1, and 0.1), respectively, and suitable ratios of cytochrome P450 monooxygenase inducer to the organophosphates are greater than or equal to about 0.1/1, 1/1, and 0.8/1 (preferably about 2/1, 8/1, and 10/1), respectively. For control of brown dog ticks, a suitable concentration of coumaphos is greater than or equal to about 0.03% (preferably greater than or equal to about 0.07%), with a suitable concentration of cytochrome P450 monooxygenase inducer greater than or equal to about 0.5% (preferably greater than or equal to about 1%). For control of typical strains of horn flies, suitable concentrations of diazinon, fenthion, pirimiphos-methyl, and chlorpyrifos are about 1.0, 10, 5, and 40 µg/cm$^2$ (measured on the area of the treated surface or animal), respectively, with the ratio of cytochrome P450 monooxygenase inducer to the organophosphate greater than or equal to about 0.125/1.

To be effective, the composition is applied directly to the target ticks or flies (i.e., larvae, pupae/nymphs, and/or adults), or to the locus of these pests. Because the composition is used as a contact poison, any method of topical application, such as direct spraying on the pest or on a substrate which is likely to be contacted by the pest, would be appropriate. However, in the preferred embodiment for treating host animals infested or suspected of being infested with the ticks or flies, the composition would be topically applied onto the exterior surfaces of the animal. In this embodiment, the composition is preferably applied by spraying, pouring, dipping, rubbing, dusting, oiling, or ear tagging (the composition being incorporated into a conventional ear tag). The process may be used for the treatment of a variety of animals, including livestock, wild animals, and domestic animals, particularly bovine, canine, equine, and Cervidae.

Although in the preferred embodiment the cytochrome P450 inducer monooxygenase inducer and the organophosphate pesticide are formulated into a single composition, in the alternative it is understood that these compounds may be formulated in separate compositions. When formulated separately, the compositions are applied in the same locus of the target ticks or flies, and thus in close proximity of one another such that both compositions are contacted by the same population of the pests. In accordance with this alternate embodiment, a first composition of one of the cytochrome P450 inducer monooxygenase inducer or the organophosphate pesticide is applied directly to the target ticks or flies or to the locus of these pests (including application onto a host animal) as described above. A second composition of the other component may then be applied to the same target ticks or flies or the same locus either simultaneously with, or following the application of the first composition.

The following examples are intended only to further illustrate the invention and are not intended to limit the scope of the invention which is defined by the claims.

EXAMPLE 1

Bioasssays were conducted to demonstrate the effect of atrazine and propazine on the toxicity of several organophosphate insecticides/acaracides against the horn fly.

The horn fly strain used in this trial (referred to as the Kerrville strain) is an in vitro strain being maintained on citrated bovine blood, and serves as a susceptible reference strain. Adult flies were exposed to organophosphate pesticide alone or in combination with varying ratios of atrazine or propazine (shown in FIGS. 1–8). Concentrations of diazinon, pirimiphos-methyl, chlorpyrifos and coumaphos were 2.8, 3.0, 8.0, and 10 µg/cm$^2$, respectively (measured as the amount of pesticide applied per unit area of filter paper). Compounds were dissolved in acetone and applied onto filter paper, which was then placed into petri dishes with the adult flies and held at room temperature under normal lighting conditions. Flies were examined for mortality after 2 hours. The results are shown in FIGS. 1–8.

Atrazine had a significant synergistic effect on diazinon activity even at low atrazine/diazinon ratios (0.25/1). Propazine had a similar effect, although somewhat weaker than atrazine. Both atrazine and propazine synergized the toxicity of pirimiphos-methyl. In contrast, neither atrazine nor propazine had any effect on the toxicity of chlorpyrifos, and both actually reduced the toxicity of coumaphos against the horn fly.

EXAMPLE 2

The bioassays of Example 1 were repeated using an in vivo strain (referred to as the Oklahoma strain) maintained on steers. This horn fly strain was established using eggs from flies collected from cattle at an Oklahoma State University research ranch. The strain is maintained in vivo on steers at the USDA-ARS-KBUSLIRL, and has been challenged with diazinon. Conditions for the bioassay were the same as Example 1 except for the addition of the organophosphate fenthion, and the triazine synergists were applied as a 1% w/v solution. The concentrations of pesticides used and the results are shown in FIGS. 9–18.

The effect of atrazine and propazine on diazinon, pirimiphos-methyl, chlorpyrifos, and coumaphos were substantially as described in Example 1 except that atrazine and propazine did synergize the toxicity of chlorpyrifos at very high chlorpyrifos levels (140.2 µg/cm$^2$ and above).

EXAMPLE 3

Bioasssays were conducted to demonstrate the effect of atrazine and propazine on the toxicity of several organophosphate insecticides/acaracides against a highly coumaphos-resistant strain of cattle fever ticks.

The strain used in these bioassays was the San Roman strain of the southern cattle tick (*Boophilus microplus*). This strain exhibits the highest resistance to coumaphos of all strains tested. The FAO larval packet test (LPT) was used to measure the susceptibility of tick larvae to acaricides. Dilutions of acaricide were prepared, dissolving the acaricide in trichloroethylene, then mixed with olive oil (ratio=2:1). A volume of 0.7 ml of the dilution was applied uniformly onto a piece of filter paper, and allowed to dry for 2 hr (trichloroethylene evaporates). The treated filter papers were folded into "packets" using bulldog clips, and approximately 100 larvae were added into each of "pockets", which were then kept in a incubator (27° C., 90% RH) for 24 h before reading (# of dead and alive were counted under a magnifying glass).

Figure 19:
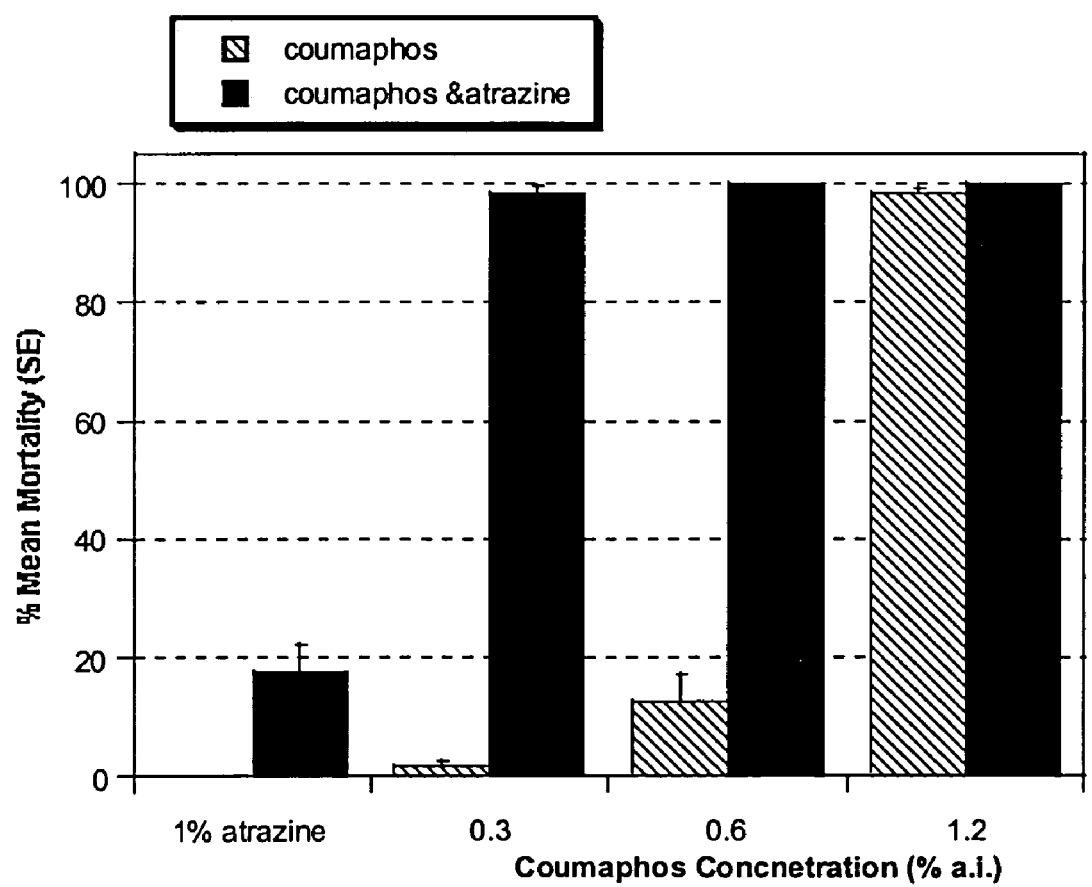
FIGS. 19–23 show the results of Example 3, demonstrating the effect of atrazine and propazine on the toxicity of several organophosphate insecticides/acaracides against a highly coumaphos-resistant strain of cattle fever ticks.
Figure 20:
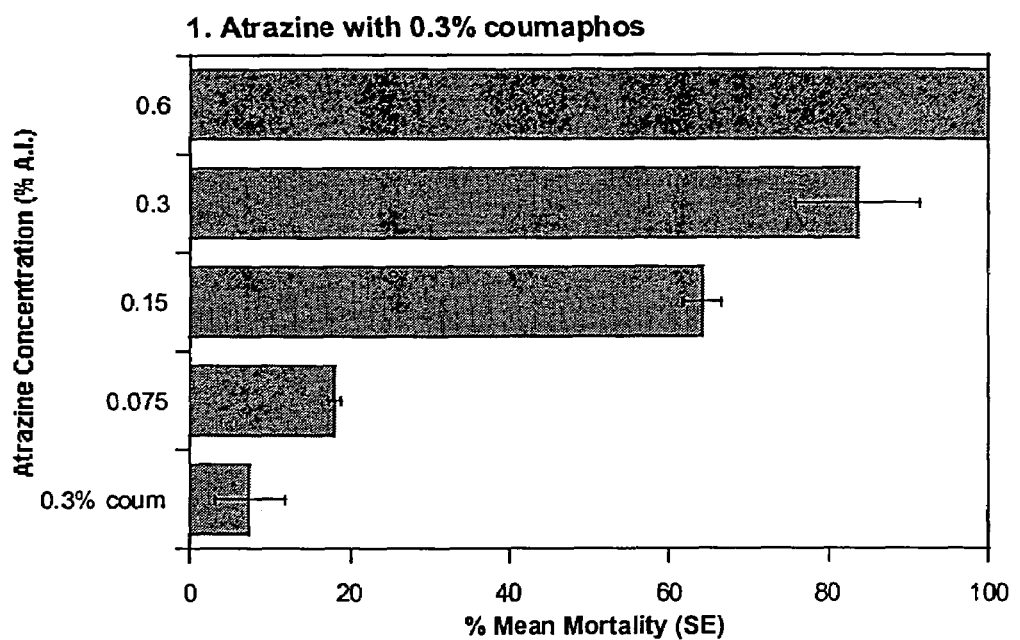
Figure 21:
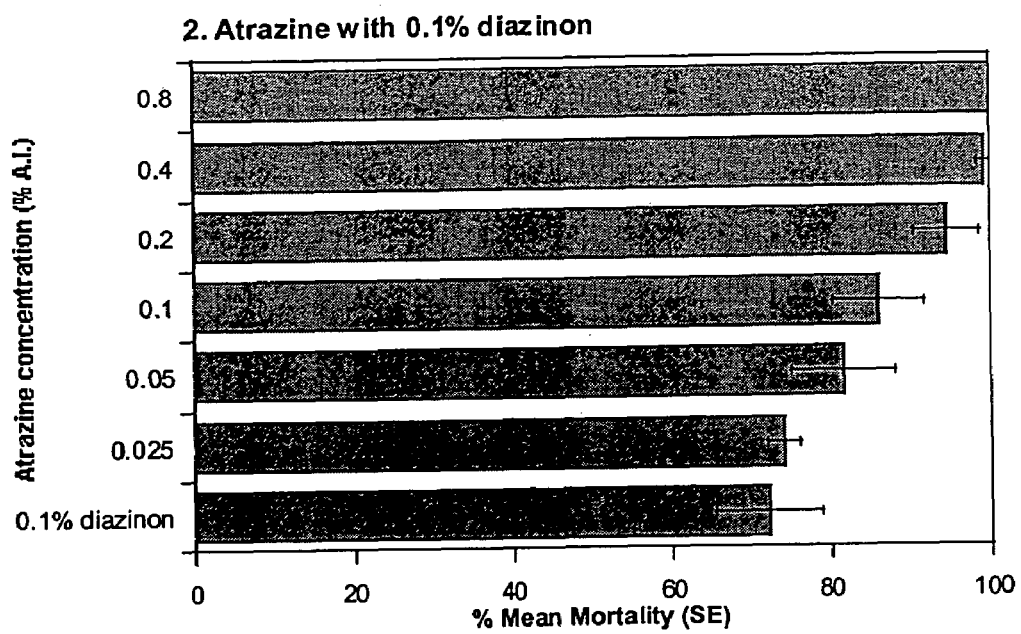
Figure 22:
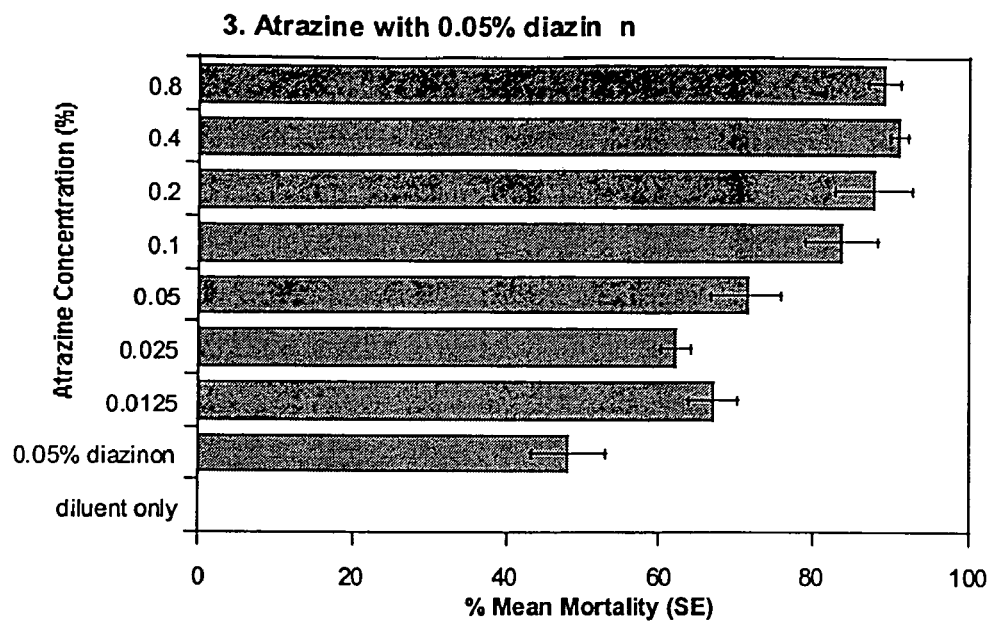
Figure 23:
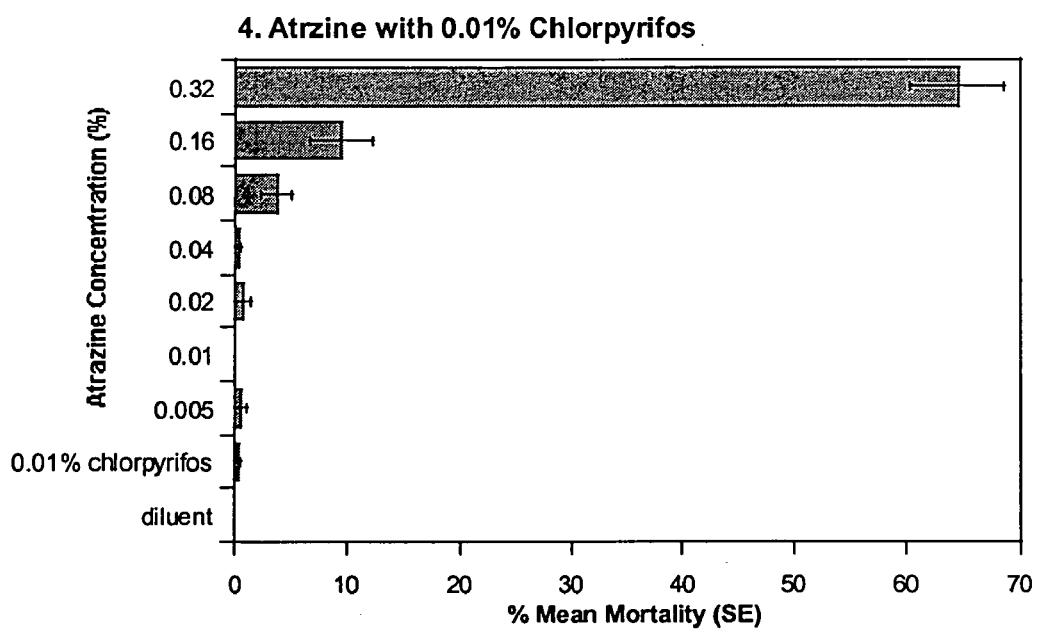

In a first trial, tick larvae were exposed to 1% atrazine alone or in combination with 0.3, 0.6, or 1.2% w/v coumaphos. The results are shown in FIG. 19. The 0.3% concentration of coumaphos which would typically be expected to kill 100% of the larvae of coumaphos-sensitive strains had virtually no effect on the larvae of this resistant strain. However, adding 1% atrazine dramatically increased coumaphos toxicity.

In a second trial, tick larvae were exposed to varying concentrations of atrazine with either 0.3% coumaphos, 0.1 or 0.05% diazinon, or 0.01% coumaphos. The results are shown in FIGS. 20–23. Atrazine strongly synergized the toxicity of 0.3% coumaphos, even at the lowest concentration of atrazine (an atrazine/coumaphos ratio of 0.25/1). 100% mortality was achieved when the atrazine/coumaphos level ratio was 2/1. Synergism was also observed between atrazine and diazinon, although the effect was weaker than that observed with coumaphos. Atrazine synergized chlorpyrifos toxicity at high atrazine/chlorpyrifos ratios (8/1 and above). It is expected that the synergistic effect would be more pronounced at higher concentrations of chlorpyrifos.

EXAMPLE 4

Another trial was performed to determine the effect of atrazine on coumaphos and diazinon toxicity against a different strain of the cattle fever tick.

Figure 24:
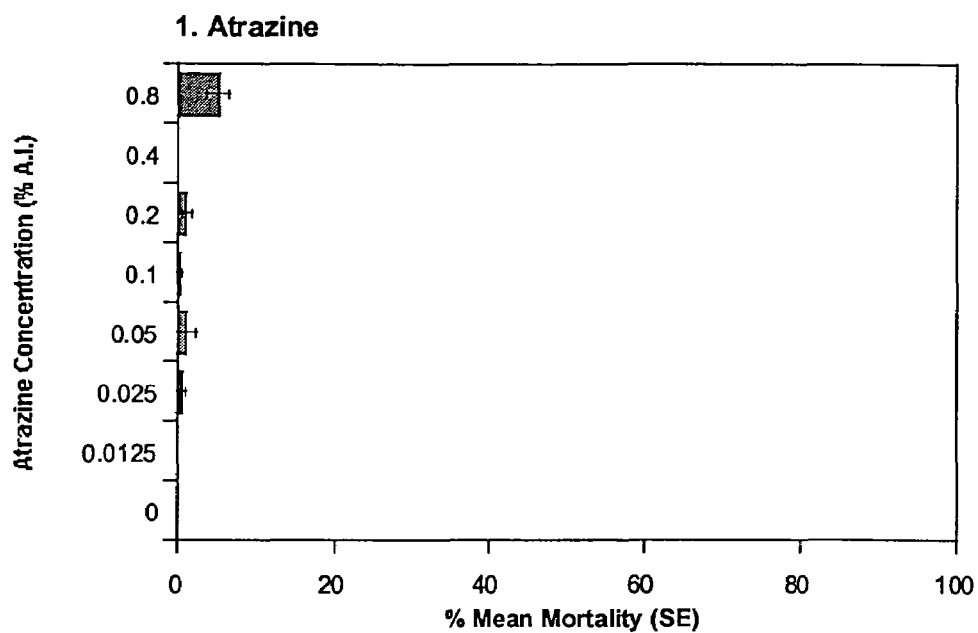
FIGS. 24–26 show the results of Example 4, demonstrating the effect of atrazine on coumaphos and diazinon toxicity against a different strain of the cattle fever tick.
Figure 25:
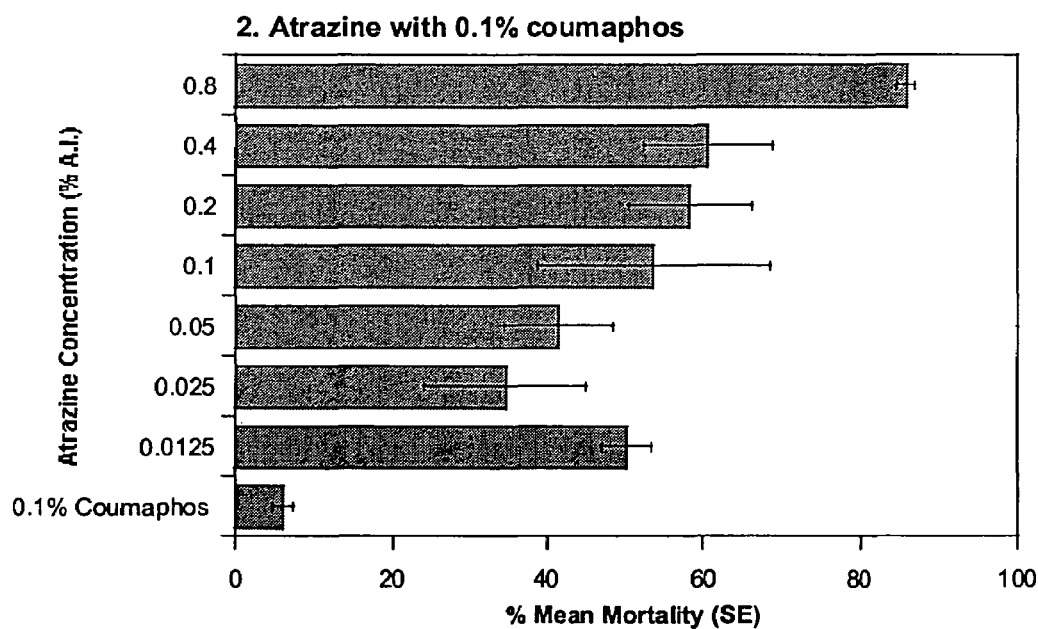
Figure 26:
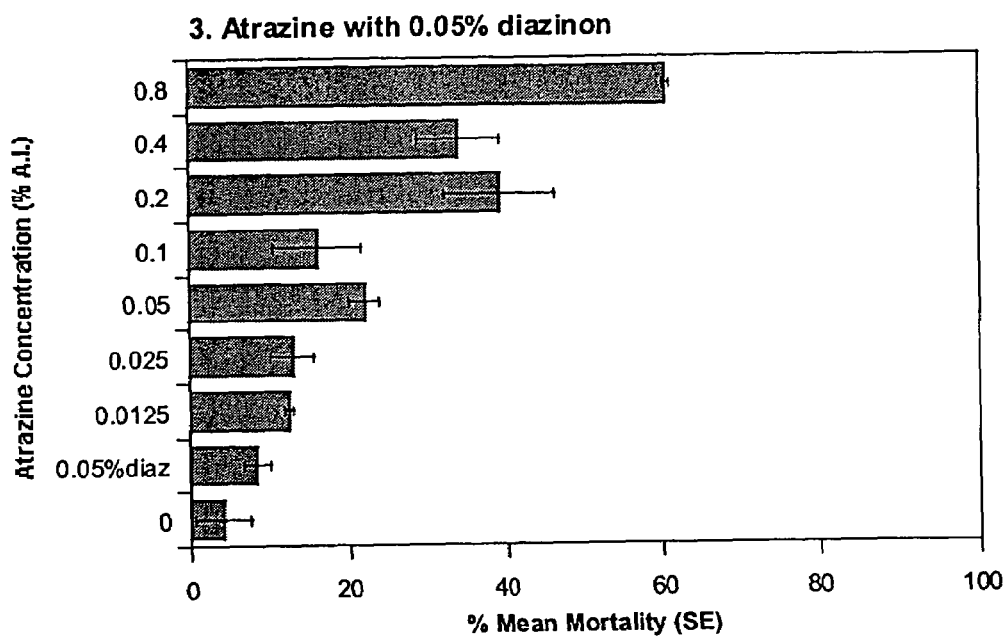

The bioassays were conducted using the same process as described in Example 3, using the San Felipe strain of the southern cattle tick. The results are shown in FIGS. 24–26.

Atrazine alone was virtually non-toxic at all concentrations except at 0.8%, at which 5.2% mortality was observed. When combined with 0.1% coumaphos, significant synergism was observed, even at the lowest atrazine/coumaphos ratio (0.125/1). A similar pattern of synergism was observed between atrazine and diazinon. Although the degree of synergism appeared to be less than observed with coumaphos, the concentration of diazinon used in the trials was only 0.05%.

EXAMPLE 5

Additional trials were performed to determine the effect of atrazine on coumaphos and diazinon toxicity against another, multiple pesticide-resistant strain of the cattle fever tick.

Figure 27:
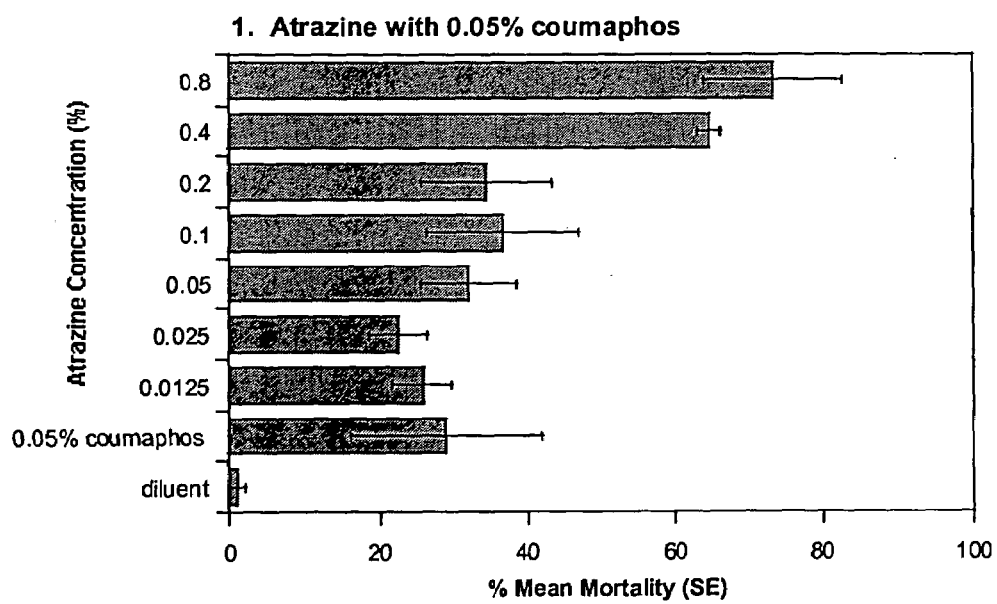
FIGS. 27 and 28 show the results of Example 5, demonstrating the effect of atrazine on coumaphos and diazinon toxicity against another, multiple pesticide-resistant strain of the cattle fever tick.
Figure 28:
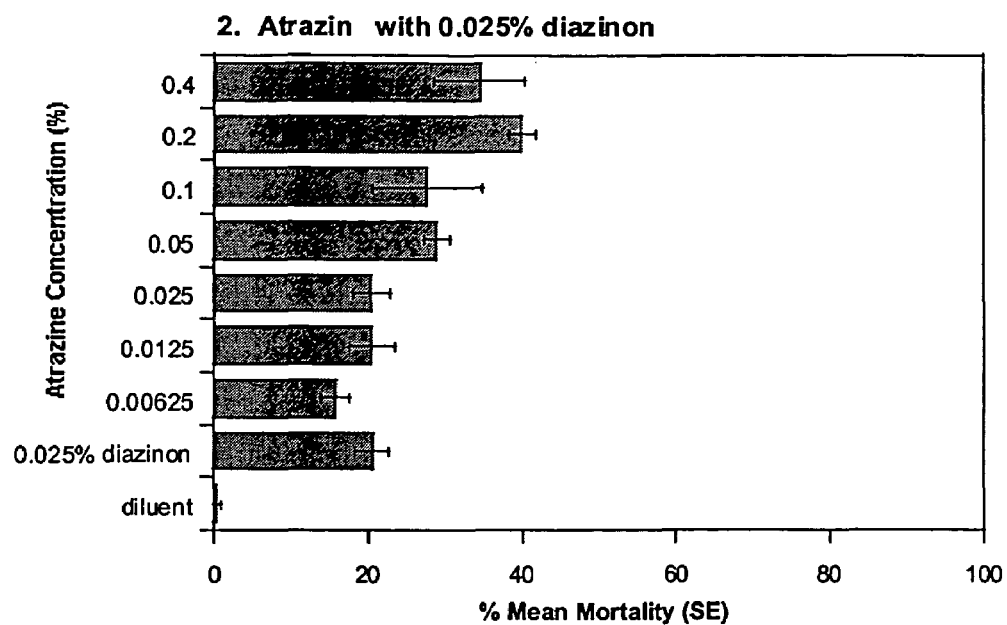

The bioassays were conducted using the same process as described in Examples 3 and 4, using the Santa Luiza strain of the southern cattle tick, which exhibits 5.5-fold resistance to coumaphos, 2.6-fold resistance to diazinon, 70-fold resistance to amitraz, and 200-fold resistance to permethrin. The results are shown in FIGS. 27 and 28.

At the concentration of 0.05%, coumaphos alone caused only 28.9% mortality. Significant synergism was observed when atrazine was combined with coumaphos at ratios of 2/1 and above. Synergism was also observed between atrazine and diazinon (0.025%) at ratios similar to that observed with coumaphos, although to a lesser extent.

EXAMPLE 6

Further trials were performed to determine the effect of atrazine on coumaphos and diazinon toxicity against yet another, multiple pesticide-resistant strain of the cattle fever tick.

Figure 29:
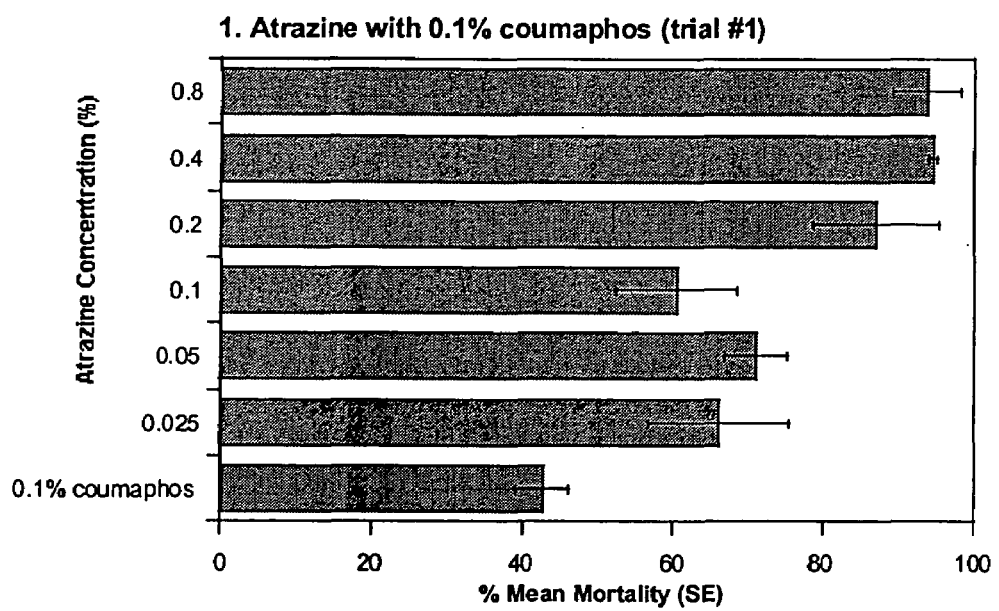
FIGS. 29–31 show the results of Example 6, demonstrating the effect of atrazine on coumaphos and diazinon toxicity against yet another, multiple pesticide-resistant strain of the cattle fever tick.
Figure 30:
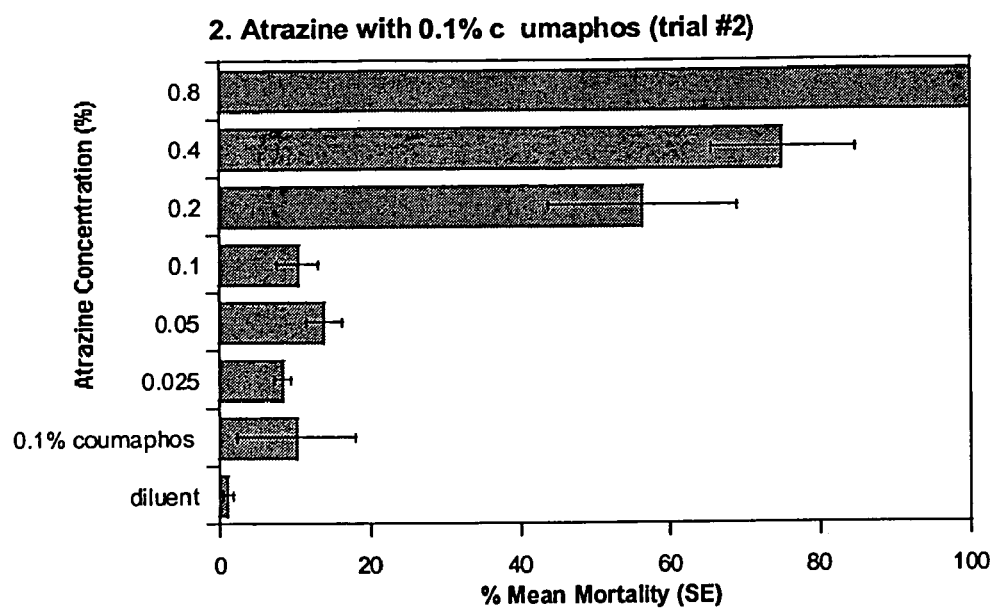
Figure 31:
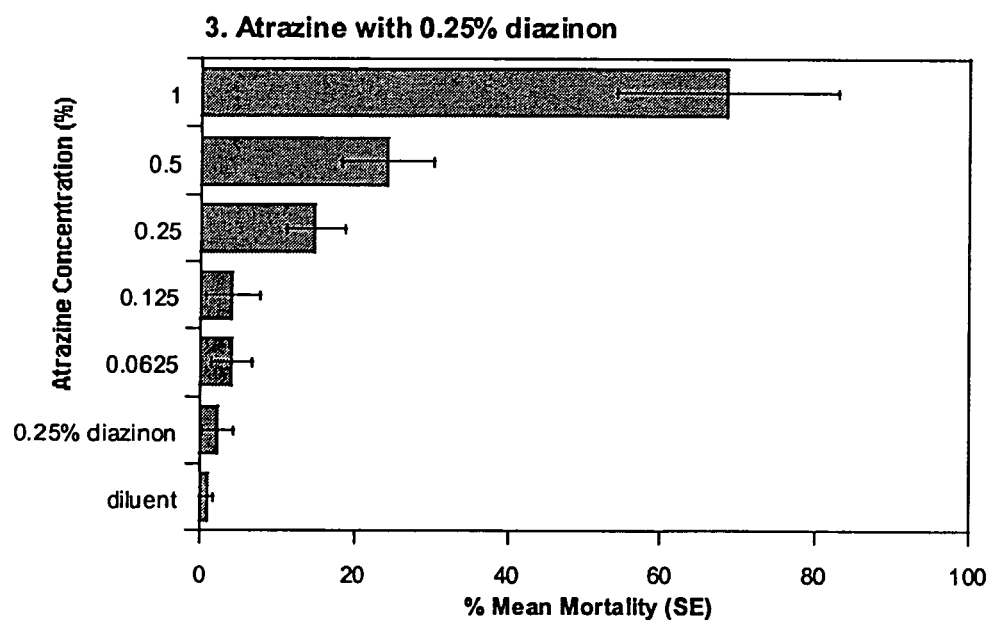

The bioassays were conducted using the same process as described in Examples 3 and 4, using the Pesqueria strain of the southern cattle tick, which exhibits low resistance to coumaphos but a very high level of resistance to diazinon. The results are shown in FIGS. 29–31.

Two sets of coumaphos assays were conducted. In the first trial, a concentration of 0.1% coumaphos (alone) gave 42.6% mortality, higher than would be typically expected. The trial was repeated, and a 10.1% mortality was obtained. In both trials, coumaphos toxicity was significantly enhanced when the atrazine/coumaphos ratio was 2/1 and above. Atrazine also significantly enhanced the toxicity of 0.25% diazinon, yielding a similar pattern of synergism.

EXAMPLE 7

Further trials were performed to determine the effect of atrazine on coumaphos, diazinon and chlorpyrifos toxicity against a pesticide-sensitive reference strain of the cattle fever tick.

Figure 32:
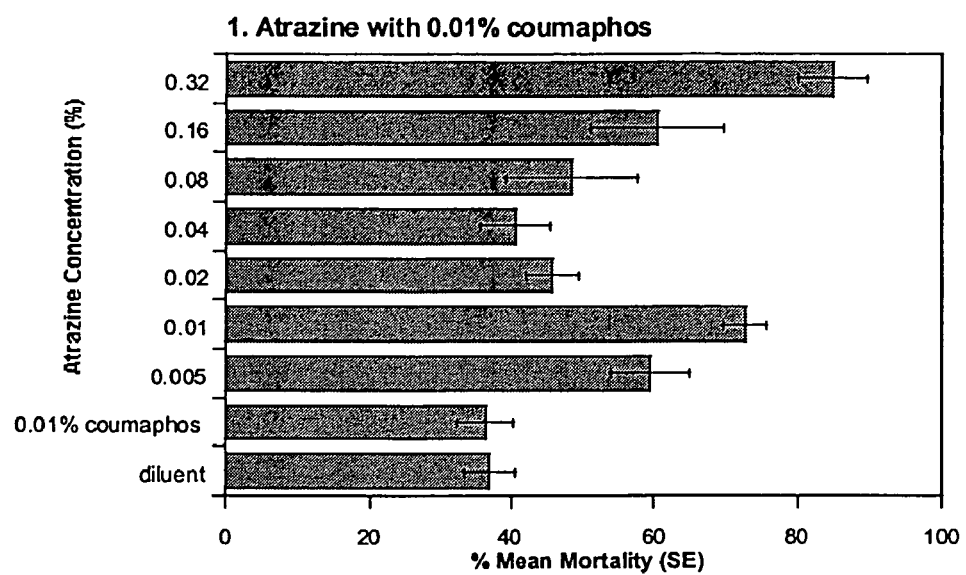
FIGS. 32–34 show the results of Example 7, demonstrating the effect of atrazine on coumaphos, diazinon and chlorpyrifos toxicity against a pesticide-sensitive reference strain of the cattle fever tick.
Figure 33:
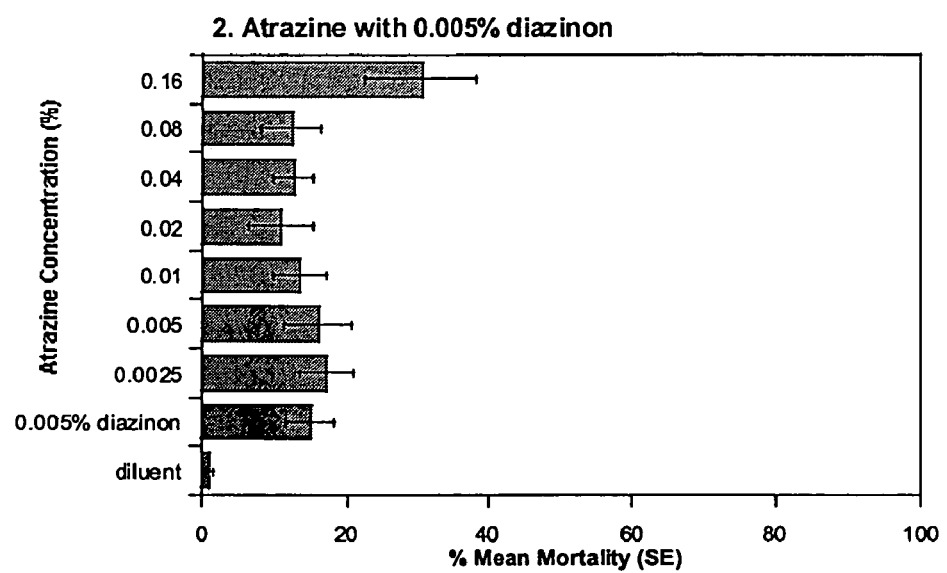
Figure 34:
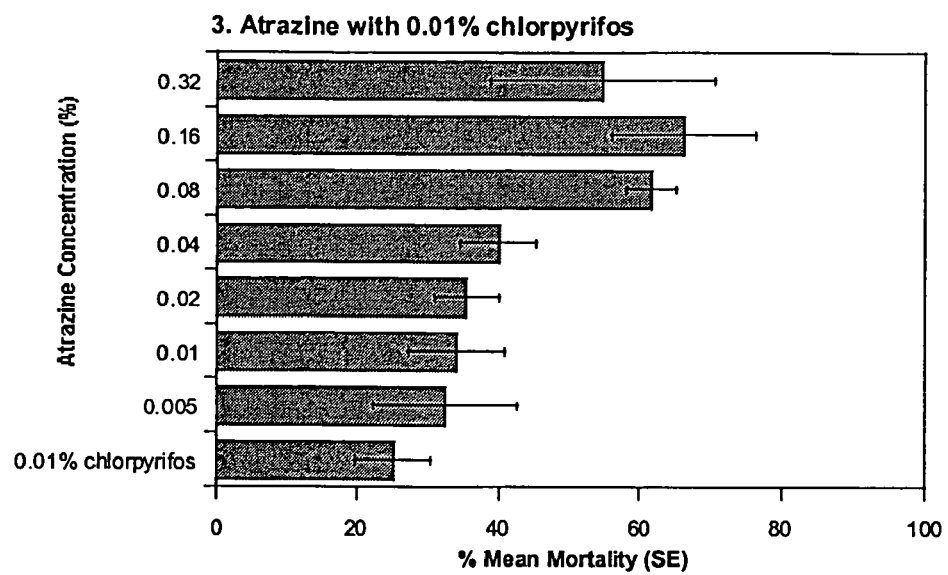

The bioassays were conducted using the same process as described in Examples 3 and 4, using the Munoz strain of the southern cattle tick, which exhibits high sensitivity to organophosphate and other acaricides. The results are shown in FIGS. 32–34.

Low concentrations of coumaphos (0.01%) resulted in 36% mortality, similar to the control. However, combinations with atrazine exhibited varying levels of synergism. When combined with very low levels of diazinon (0.005%) atrazine only provided a synergistic effect at high atrazine/diazinon ratios (32/1). In contrast, at higher diazinon concentrations (0.05%), the synergistic effect of atrazine was observed even at low atrazine/diazinon ratios (data not shown). Atrazine also significantly enhanced the toxicity of 0.01% chlorpyrifos.

EXAMPLE 8

Bioasssays were conducted to demonstrate the effect of atrazine on the toxicity of coumaphos against the brown dog tick.

Figure 35:
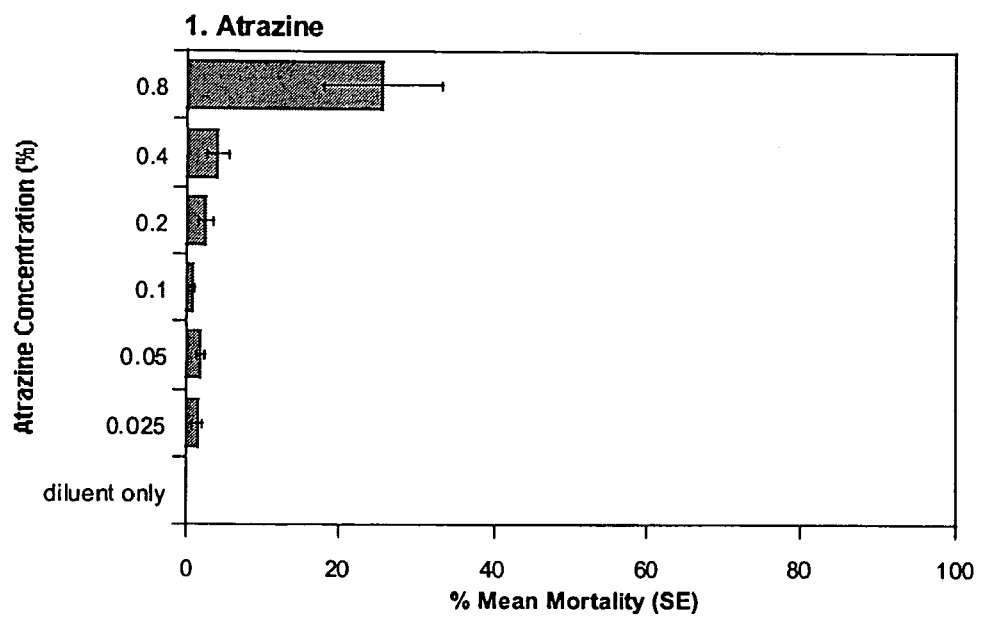
FIGS. 35–37 show the results of Example 8, demonstrating the effect of atrazine on the toxicity of coumaphos against the brown dog tick.
Figure 36:
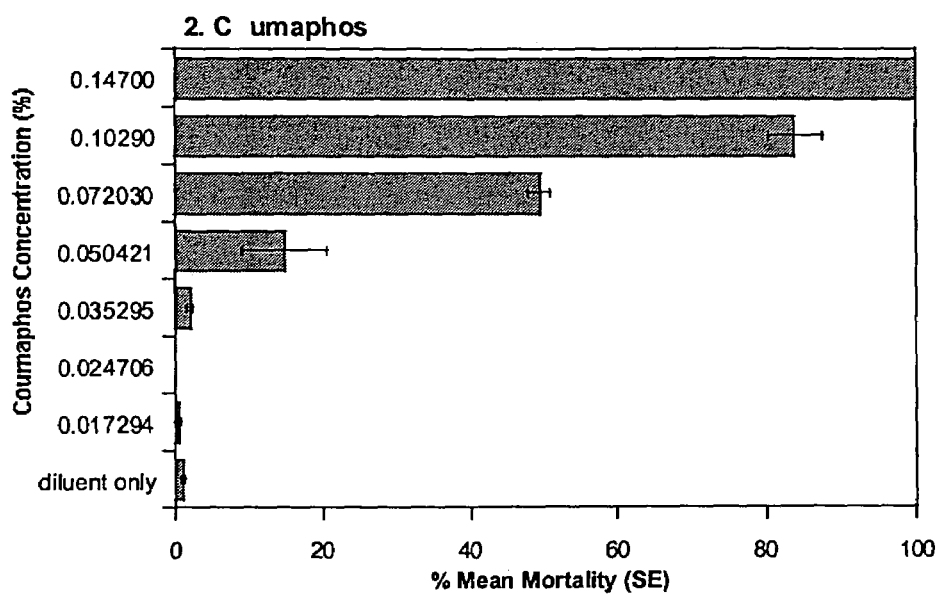
Figure 37:
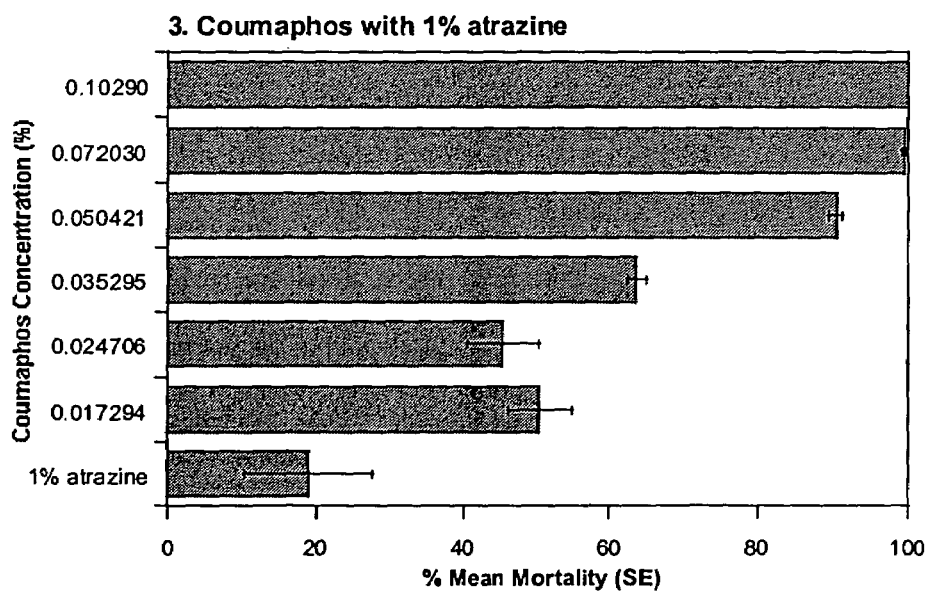

The bioassays were conducted using the same process as described in Examples 3 and 4. The results are shown in FIGS. 35–37.

Atrazine alone had very low toxicity (less than 4% mortality) toward tick larvae at low doses, at or below 0.4%. Higher concentrations of atrazine, 0.8 and 1.0%, resulted 25.7 and 18.9% mortality, respectively. Coumaphos had no effect on larvae at low concentrations (less than or equal to 0.035%), while mortality increased with higher coumaphos concentrations. Significant synergism was observed when atrazine (1%) was combined with coumaphos. The concentration of 0.035% coumaphos caused greater than 60% mortality when used with the synergist atrazine. It is expected that significant synergism would also be observed using lower atrazine concentrations.

It is understood that the foregoing detailed description is given merely by way of illustration and that modifications and variations may be made therein without departing from the spirit and scope of the invention.

We claim:

1. A method for controlling pests, comprising applying a cytochrome P450 monooxygenase inducer and an organophosphate pesticide to the locus of said pests, wherein said pests are ticks and said cytochrome P450 monooxygenase inducer and said organophosphate pesticide are applied in an amount such that the combination thereof is present in a pesticidally effective amount.

2. The method of claim 1 wherein said organophosphate pesticide is selected from the group consisting of coumaphos, diazinon, chlorpyrifos, fenthion, and pirimiphos-methyl.

3. The method of claim 1 wherein said cytochrome P450 monooxygenase enhancer is a triazine.

4. The method of claim 3 wherein said cytochrome P450 monooxygenase enhancer is selected from the group consisting of atrazine, propazine, and simazine.

5. The method of claim 1 wherein said combination of said cytochrome P450 monooxygenase inducer and said organophosphate pesticide is selected from the group consisting of atrazine with coumaphos, atrazine with diazinon, atrazine with chlorpyrifos, propazine with diazinon, atrazine with fenthion, atrazine with pirimiphos-methyl, and propazine with pirimiphos-methyl.

6. The method of claim 1 wherein said pests are selected from the group consisting of cattle fever ticks (*Boophilus annulatus* and *B. microplus*) and the brown dog tick (*Rhipicephalus sanuineus*).

7. The method of claim 6 wherein said cytochrome P450 monooxygenase inducer is applied in an amount effective to synergistically increase the pesticidal activity of said organophosphate pesticide.

8. The method of claim 1 wherein said applying comprises applying said cytochrome P450 monooxygenase inducer and said organophosphate pesticide onto an animal host of said pests.

9. The method of claim 8 wherein said animal is selected from the group consisting of livestock, wild animals, and domestic animals.

10. The method of claim 8 wherein said animal is selected from the group consisting of bovine, canine, equine, and Cervidae.

11. The method of claim 8 wherein said applying said cytochrome P450 monooxygenase inducer and said organophosphate pesticide onto an animal comprises spraying, pouring, dipping, rubbing, dusting, oiling, or ear tagging.

12. The method of claim 11 wherein said cytochrome P450 monooxygenase inducer and said organophosphate pesticide are formulated in the same composition.

13. The method of claim 12 wherein said composition further comprises an inert carrier selected from the group consisting of alcohols, ethers, hydrocarbons, halogenated hydrocarbons, glycols, ketones, esters, oils, clays, kaolinite, silicas, cellulose, rubber, talc, vermiculate, synthetic polymers, controlled release microparticles, and controlled release microcapsules.

14. The method of claim 1 wherein said cytochrome P450 monooxygenase inducer and said organophosphate pesticide are formulated in separate compositions.

15. The method of claim 1 wherein said cytochrome P450 monooxygenase inducer and said organophosphate pesticide are formulated in the same composition.

16. The method of claim 15 wherein said composition further comprises an inert carrier.

17. The method of claim 16 wherein said carrier is selected from the group consisting of alcohols, ethers, hydrocarbons, halogenated hydrocarbons, glycols, ketones, esters, oils, clays, kaolinite, silicas, cellulose, rubber, talc, vermiculate, synthetic polymers, controlled release microparticles, and controlled release microcapsules.

18. The method of claim 1 wherein said pests are selected from the group consisting of cattle fever ticks (*Boophilus annulatus* and *B. microplus*), the lonestar tick (*Amblyomma americanum*), and the brown dog tick (*Rhipicephalus sanuineus*).

* * * * *